United States Patent [19]

Schneider

[11] 4,119,650
[45] Oct. 10, 1978

[54] THROMBOXANE B DIALKYL-ACETAL DIOL INTERMEDIATES

[75] Inventor: William P. Schneider, Kalamazoo, Mich.

[73] Assignee: The Upjohn Company, Kalamazoo, Mich.

[21] Appl. No.: 830,540

[22] Filed: Sep. 6, 1977

Related U.S. Application Data

[60] Division of Ser. No. 716,473, Aug. 20, 1976, Pat. No. 4,070,384, which is a continuation-in-part of Ser. No. 676,894, Apr. 14, 1976, Pat. No. 4,018,804.

[51] Int. Cl.$^2$ ............................ C09F 7/00; C11C 3/00
[52] U.S. Cl. ...................................... 260/408; 560/55; 560/61; 560/62; 560/183; 560/184; 560/186; 260/345.7 P; 424/284; 424/312; 424/314; 424/308

[58] Field of Search ................. 260/408, 405, 410.9 P, 260/410 P, 410.5; 560/55, 61, 62, 183, 184, 186; 424/284, 308, 312, 314

[56] References Cited

PUBLICATIONS

Samuelsson, B., Proc. Nat. Acad. Sci. USA 71, pp. 3400–3404 (1974).
Heusler, K. et al. Angew., Chem. vol. 3, pp. 525–596 (1964).

*Primary Examiner*—Winston A. Douglas
*Assistant Examiner*—John F. Nichling
*Attorney, Agent, or Firm*—Robert A. Armitage

[57] ABSTRACT

The present specification provides novel intermediates and novel processes for the synthesis of various side chain and skeletal analogs of Thromboxane $B_2$ ($11\beta$-homo-$11\alpha$-oxa-PGF$_{2\alpha}$). These analogs are particularly and especially useful as reproductive cycle control agents.

1 Claim, No Drawings

THROMBOXANE B DIALKYL-ACETAL DIOL INTERMEDIATES

CROSS REFERENCE TO RELATED APPLICATION

The present application is a divisional application of Ser. No. 716,473, filed Aug. 20, 1976, now issued as U.S. Pat. No. 4,070,384; which is a continuation-in-part of Ser. No. 676,894, filed Apr. 14, 1976, issued as U.S. Pat. No. 4,018,804 on Apr. 19, 1977.

The present invention relates to processes and intermediates for Thromboxane B compounds for which the essential material constituting a disclosure therefor is incorporated by reference herein from U.S. Pat. No. 4,020,173, issued Apr. 26, 1977 and U.S. Pat. No. 4,070,384, issued Jan. 24, 1978.

I claim:

1. A thromboxane intermediate of the formula:

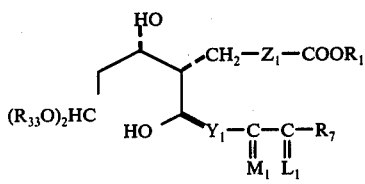

wherein
$Z_1$ is
(1) cis-$CH=CH-CH_2-(CH_2)_g-CH_2-$,
(2) cis-$CH=CH-CH_2-(CH_2)_g-CF_2-$,
(3) cis-$CH_2-CH=CH-(CH_2)_g-CH_2-$,
(4) $-(CH_2)_3-(CH_2)_g-CH_2-$,
(5) $-(CH_2)_3-(CH_2)_g-CF_2-$,
(6) $-CH_2-O-CH_2-(CH_2)_g-CH_2-$,
(7)

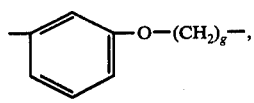

or
(8)

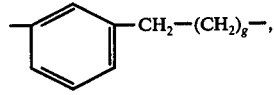

wherein $g$ is one, 2, or 3;
wherein $R_1$ is alkyl of one to 12 carbon atoms, inclusive, cycloalkyl of 3 to 10 carbon atoms, inclusive, aralkyl of 7 to 12 carbon atoms, inclusive, phenyl, phenyl substituted with one or two chloro, fluoro, or alkyl of one to 4 carbon atoms, inclusive, or a pharmacologically acceptable cation;
wherein $Y_1$ is trans-$CH=CH-$ or $-CH_2CH_2-$;
wherein $M_1$ is

-continued
or

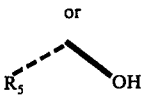

wherein $R_5$ is hydrogen or methyl;
wherein $L_1$ is

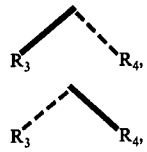

or a mixture of

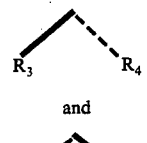

and

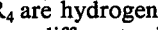

wherein $R_3$ and $R_4$ are hydrogen, methyl, or fluoro, being the same or different with the proviso that one of $R_3$ and $R_4$ is methyl only when the other is hydrogen or methyl; and
wherein $R_7$ is
(1) $-(CH_2)_m-CH_3$,
(2)

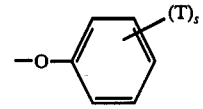

or
(3)

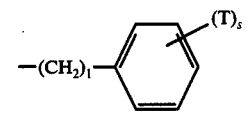

wherein $l$ is zero, one, two, or three,
wherein $m$ is one to 5, inclusive, T is alkyl of one to 3 carbon atoms, inclusive, alkoxy of one to 3 carbon atoms, inclusive, chloro, fluoro, or trifluoromethyl, and $s$ is one, two, or 3, the various T's being the same or different, with the proviso that not more than two T's are other than alkyl, with the further proviso that $R_7$ is

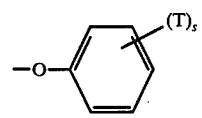

only when $R_3$ and $R_4$ are hydrogen or methyl, being the same or different; and
wherein $R_{33}$ is alkyl of one to 5 carbon atoms, inclusive.

* * * * *